(12) United States Patent
Gulev et al.

(10) Patent No.: US 11,399,813 B2
(45) Date of Patent: Aug. 2, 2022

(54) BIOPSY SYRINGE

(71) Applicant: TOTLE DEVELOPMENT APS, Hillerød (DK)

(72) Inventors: Morten Gulev, Rønne (DK); Karsten Videbaek, Jyllinge (DK); Bjarne Andersen, Frederikssund (DK); Per Rosenberg Jensen, Holmegaard (DK)

(73) Assignee: TOTLE DEVELOPMENT APS, Hillerod (DK)

( * ) Notice: Subject to any disclaimer, the term of this patent is extended or adjusted under 35 U.S.C. 154(b) by 829 days.

(21) Appl. No.: 16/072,311

(22) PCT Filed: Jan. 27, 2017

(86) PCT No.: PCT/EP2017/051753
§ 371 (c)(1),
(2) Date: Jul. 24, 2018

(87) PCT Pub. No.: WO2017/129735
PCT Pub. Date: Aug. 3, 2017

(65) Prior Publication Data
US 2019/0029657 A1    Jan. 31, 2019

(30) Foreign Application Priority Data

Jan. 28, 2016 (DK) .......................... PA 2016 70045

(51) Int. Cl.
*A61B 10/02* (2006.01)
*A61B 10/00* (2006.01)
(Continued)

(52) U.S. Cl.
CPC ...... *A61B 10/0283* (2013.01); *A61B 5/15003* (2013.01); *A61B 5/153* (2013.01);
(Continued)

(58) Field of Classification Search
CPC ........ A61B 5/150213; A61B 5/150221; A61B 5/150236; A61B 5/153; A61B 5/150099;
(Continued)

(56) References Cited

U.S. PATENT DOCUMENTS 4,287,819 A    9/1981 Emerit
4,549,554 A   10/1985 Markham
(Continued)

OTHER PUBLICATIONS

International Search Report and Written Opinion dated Apr. 24, 2017 by the International Searching Authority for Application No. PCT/EP2017/051753, filed Jan. 27, 2017, and published as WO 2017/129735 dated Aug. 3, 2017 (Applicant—Totle Development APS ) (10 pages).

*Primary Examiner* — Devin B Henson
*Assistant Examiner* — Huong Q Nguyen
(74) *Attorney, Agent, or Firm* — Ballard Spahr LLP (57) ABSTRACT

The present disclosure relates to a needle extraction syringe (1) for extracting fluid and/or tissue comprising: a barrel (2) having a proximal lumen (6); and a distal lumen (7) for collecting aspirated fluid/tissue; a plunger (3) having a plunger head (9) sealingly engaged inside the barrel (2); and a plunger body (10) with an internal channel (11); a valve (8) located between the plunger head (9) and a distal end of the syringe inside the barrel (2), separating the proximal lumen (6) and the distal lumen (7) such that air can only flow from the distal lumen (7) to the proximal lumen (6) in a first valve configuration; a sealing element (13) located inside the barrel (2) proximal to the plunger head (9), wherein the plunger head (9) and the sealing element (13) define a vacuum chamber (14) having a variable volume therebetween, wherein the vacuum chamber (14) and the internal channel (11) are fluidly disconnected in relation to each other in a first configuration of the syringe and fluidly connected in a second configuration of the syringe.

14 Claims, 6 Drawing Sheets

(51) Int. Cl.
*A61B 5/15* (2006.01)
*A61B 5/153* (2006.01)

(52) U.S. Cl.
CPC .. *A61B 5/150213* (2013.01); *A61B 5/150221* (2013.01); *A61B 5/150236* (2013.01); *A61B 5/150244* (2013.01); *A61B 10/0045* (2013.01); *A61B 10/0233* (2013.01)

(58) Field of Classification Search
CPC ........ A61B 5/150244; A61B 5/150251; A61B 10/0283; A61B 2010/045; A61M 2005/3128; A61M 5/3129; A61M 5/3134; A61M 5/3135; A61M 5/3148; A61M 5/315; A61M 5/3156; A61M 1/0003; A61M 1/0066; A61M 1/0068; A61M 1/007; A61M 1/08; A61M 5/178; A61M 5/19

See application file for complete search history.

(56) References Cited

U.S. PATENT DOCUMENTS

| | | | | |
|---|---|---|---|---|
| 4,640,297 A | * | 2/1987 | Bates | B01L 3/0217 |
| | | | | 600/578 |
| 4,813,433 A | | 3/1989 | Downey | |
| 5,277,198 A | | 1/1994 | Kanner et al. | |
| 6,234,980 B1 | * | 5/2001 | Bell | A61B 17/1322 |
| | | | | 600/578 |
| 7,048,720 B1 | * | 5/2006 | Thorne, Jr. | A61M 5/284 |
| | | | | 604/191 |
| 2013/0317447 A1 | * | 11/2013 | Cowe | A61M 5/2033 |
| | | | | 604/196 |

\* cited by examiner

BIOPSY SYRINGE

CROSS-REFERENCE TO RELATED APPLICATIONS

This application is a U.S. National Phase Application of International Application No. PCT/EP2017/051753, filed Jan. 27, 2017, which claims priority to Danish Patent Application No. PA 2016 70045, filed Jan. 28, 2016, each of which are hereby incorporated by reference in their entirety.

The present disclosure relates to a biopsy syringe, such as a needle extraction syringe for extracting fluid and/or tissue from a patient and, optionally, exhausting the aspirated fluid/tissue from the syringe.

BACKGROUND OF INVENTION

Biopsy, such as fine-needle aspiration biopsy (FNAB or FNA), fine-needle aspiration cytology (FNAC), or core needle biopsy (CNB), is a diagnostic procedure used to remove samples of tissue or fluid from an organ of the body or a lump found under the skin. Fine-needle aspiration may also be done to identify the type of cells inside a lump or to see how well treatment of an existing lump is working. FNA is commonly used to investigate lumps found in the breast or thyroid (a gland found in your neck) but it can also be used in other parts of the body. A core needle biopsy (CNB) is much like an FNAB. A slightly larger, hollow needle is used to withdraw small cylinders (or cores) of tissue. A CNB is most often done in the health care provider's office with local anesthesia. The needle is put in 3 to 6 times to get the samples, or cores. This takes longer than an FNAB, but it is more likely to give a clear result because more tissue is taken to be checked. These are very useful ways of detecting cancer. One biopsy technique used to evaluate breast tissue involves inserting a biopsy probe into the breast tissue region of interest to capture one or more tissue samples from the region. Such a biopsy technique may utilize a vacuum to pull the tissue to be sampled into a sample notch of the biopsy probe, after which the tissue is severed and collected. A thin, hollow needle or cannula is inserted through the skin into the region of interest. Typically there is a syringe attached to the needle. By pulling the plunger out from the barrel of the syringe, thereby creating a vacuum in the needle, the syringe can be used to aspirate the samples into the needle and further into the barrel.

During fine-needle aspiration, typically the barrel and plunger of the syringe are held in one hand while the other hand guides the needle. Maintaining the needle in the right position in relation to the object to be sampled is a difficult task and requires precision. At the same time the plunger of the syringe has to be pulled using the other hand, which also requires precision. Operating the plunger using only one hand is difficult, given that the barrel has to be held, and, at the same time, the plunger has to be pushed or pulled out from the barrel using the same hand, which also requires a precise amount of pressure or force.

Alternatively, the syringe barrel can be held in one hand while the other hand pulls the plunger of the syringe, thereby creating vacuum in the needle to capture tissue samples. This technique ensures better control of the required amount of pressure or force to pull out the plunger from the barrel in order to aspirate tissue samples accurately. However, since there is no hand to guide the needle, there is risk that the needle is not positioned accurately. This may imply that the right sample tissue is not aspirated and the fine-needle process will have to be repeated, or, in the worst case, a false negative result is obtained, which can delay diagnosis.

SUMMARY OF INVENTION

The present disclosure relates to a biopsy syringe, such as a needle extraction syringe, designed to be more conveniently operated than the existing solution. In particular, the disclosed solution allows for single-handed generation of vacuum inside the syringe and ergonomic generation of vacuum by pushing the plunger instead of pulling it. The disclosure relates to an improved biopsy device designed for single-hand operation and/or with integrated sampling chamber.

In a first embodiment, the present disclosure relates to a needle extraction syringe (1) for extracting fluid and/or tissue comprising:
- a barrel (2) having:
  - a proximal lumen (6); and
  - a distal lumen (7) for collecting aspirated fluid/tissue;
- a plunger (3) having:
  - a plunger head (9) sealingly engaged inside the barrel (2); and
  - a plunger body (10) with an internal channel (11);
- a valve (8) located between the plunger head (9) and a distal end of the syringe inside the barrel (2), separating the proximal lumen (6) and the distal lumen (7) such that air can only flow from the distal lumen (7) to the proximal lumen (6) in a first valve configuration;
- a sealing element (13) located inside the barrel (2) proximal to the plunger head (9), wherein the plunger head (9) and the sealing element (13) define a vacuum chamber (14) having a variable volume therebetween, wherein the vacuum chamber (14) and the internal channel (11) are fluidly disconnected in relation to each other in a first configuration of the syringe and fluidly connected in a second configuration of the syringe.

The syringe typically has a tip (4) and a first hollow needle or cannula (5) at a distal end of the syringe (1). The first hollow needle/cannula (5) may be a removable needle and/or a rotatable needle. The valve may comprise a membrane (21).

Unlike the devices known in the art, the presently disclosed needle extraction syringe (1) can create a vacuum inside the barrel (2) by pushing the plunger (3) downwards towards the distal end of the barrel (2), i.e. the end typically having a hollow needle attached. One possible single-handed grip is consequently closing the index-, middle-, ring- and little fingers around the barrel while the thumb is relatively loose. Typically the little finger is placed on the distal part of the syringe (1) towards the needle and the index finger on the upper part towards the proximal part. With such a grip the thumb is typically stronger and more precisely moved downwards towards the palm of the user.

The principle of the presently disclosed needle extraction syringe (1), allowing for the creation of vacuum inside the barrel (2) by pushing the plunger (3) towards the distal end of the syringe instead of drawing it away from the distal end towards the proximal end of the syringe, involves the use of a plunger having a plunger head (9) sealingly engaged inside the barrel and a plunger body (10) with an internal channel (11). The plunger body (11) may be e.g. a hollow shaft. The closed volume on the proximal side of the plunger head constitutes a vacuum chamber (14) having a variable volume. The volume is defined by the plunger head (9), the plunger body (10) and a sealing (13) of the proximal end of the syringe. When the plunger head (9) is pushed in the direction towards the distal end of the syringe, the vacuum chamber (14) is mechanically expanded. In this configuration the vacuum chamber (14) and the internal channel (11) are isolated i.e. fluidly disconnected in relation to each other, which creates a vacuum in the vacuum chamber (14) when it expands. In this configuration, the air in the distal lumen (7) is typically pushed out through the plunger body (10), leaving the syringe (1). When the plunger has been pushed beyond a predefined limit in the longitudinal direction of the syringe towards the distal end of the syringe, it enters the second configuration, wherein the vacuum chamber (14) and the internal channel (11) are fluidly connected and the internal channel (11) does not have a connection to the outside of the syringe.

In one embodiment, this mechanism is achieved by a side channel (16), preferably being part of the plunger body (11). In the first configuration, the side channel (16) is located longitudinally displaced from the vacuum chamber (14), thereby connecting the internal channel (11) with the outside atmospheric pressure of the syringe. When the plunger moves towards the distal end of the syringe, vacuum is built up inside the vacuum chamber (14), and at some point the side channel (16) enters the level in the longitudinal direction of the syringe where it is in level with the vacuum chamber (14), thereby fluidly connecting the vacuum chamber (14) and the internal channel (11). In this configuration, air flows from the distal lumen (7), possible also from a variable proximal lumen volume (15), to the vacuum chamber (14).

These and other aspects of the invention are set forth in the following detailed description of the invention.

DETAILED DESCRIPTION OF THE INVENTION

As stated, the present disclosure relates to a needle extraction syringe (1) for extracting fluid and/or tissue comprising:
a barrel (2) having:
  a proximal lumen (6); and
  a distal lumen (7) for collecting aspirated fluid/tissue;
a plunger (3) having:
  a plunger head (9) sealingly engaged inside the barrel (2); and
  a plunger body (10) with an internal channel (11);
a valve element (8) located between the plunger head (9) and a distal end of the syringe inside the barrel (2), separating the proximal lumen (6) and the distal lumen (7) such that air can only flow from the distal lumen (7) to the proximal lumen (6) in a first valve configuration;
a sealing element (13) located inside the barrel (2) proximal to the plunger head (9), wherein the plunger head (9) and the sealing element (13) define a vacuum chamber (14) having a variable volume therebetween, wherein the vacuum chamber (14) and the internal channel (11) are fluidly disconnected in relation to each other in a first configuration of the syringe and fluidly connected in a second configuration of the syringe.

The syringe, such as a fine-needle aspiration syringe, typically has a tip (4) and a first hollow needle (5) at a distal end of the syringe (1).

One feature of the fine-needle aspiration syringe (1) is that it is capable of generating vacuum, and thereby aspirating tissue, by moving the plunger towards the distal end of the barrel (2) instead of more conventionally drawing the plunger (3) away from the distal end of the barrel (2). This is achieved by a combination of structural features of the syringe (1). In one embodiment, the plunger (3) has a plunger head (9) sealingly engaged inside the barrel and a plunger body (10) with an internal channel (11). Sealingly engaged shall have the common meaning of a plunger head i.e. that as the plunger head slides in the longitudinal direction of the syringe, the contact between the plunger head and the cylindrical sidewalls of the barrel is air and liquid tight. The internal channel (11) is preferably in fluid connection with a proximal lumen (6) inside the barrel such that air can be transported through the internal channel (11) when the plunger (3) is moved in the direction towards the distal end of the syringe (1). A vacuum chamber (14) is defined on the proximal side of the plunger head (9). The vacuum chamber is defined by the space between the plunger head (9) and the proximal sealing (13) of the syringe. If the internal channel (11) is a hollow shaft of the plunger body (10), the vacuum chamber (14) may have an annular elongate shape. The proximal lumen (6) may comprise a variable proximal lumen volume (15), variable in the sense that when the plunger head is moved in the longitudinal direction of the syringe (1) the volume of the proximal lumen (6) is varied.

Figure 1A:
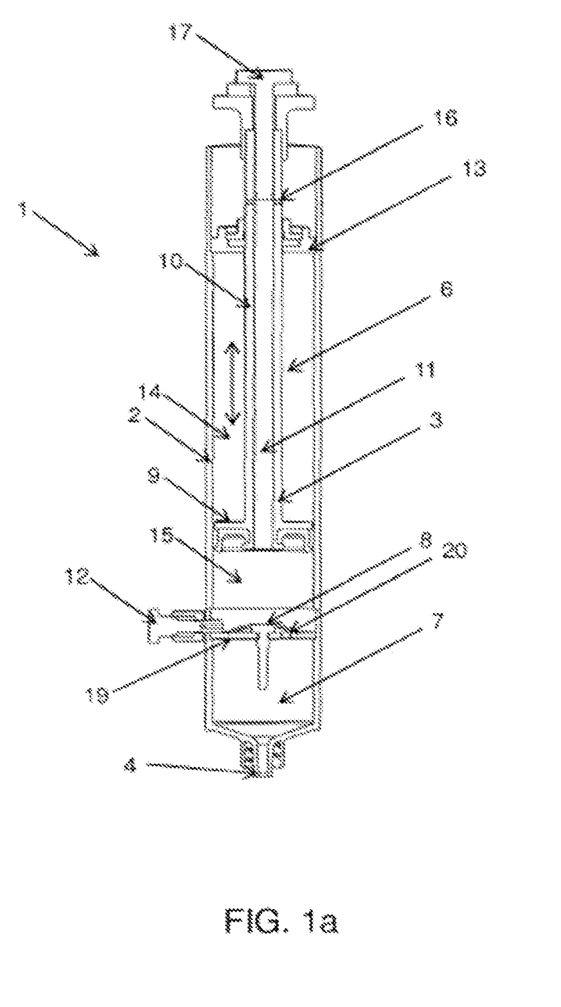
FIG. 1a shows one embodiment of the presently disclosed biopsy needle, in form of a fine-needle aspiration syringe (1) for aspirating fluid and/or tissue, in a first configuration for establishing vacuum in the vacuum chamber (14).
Figure 1B:
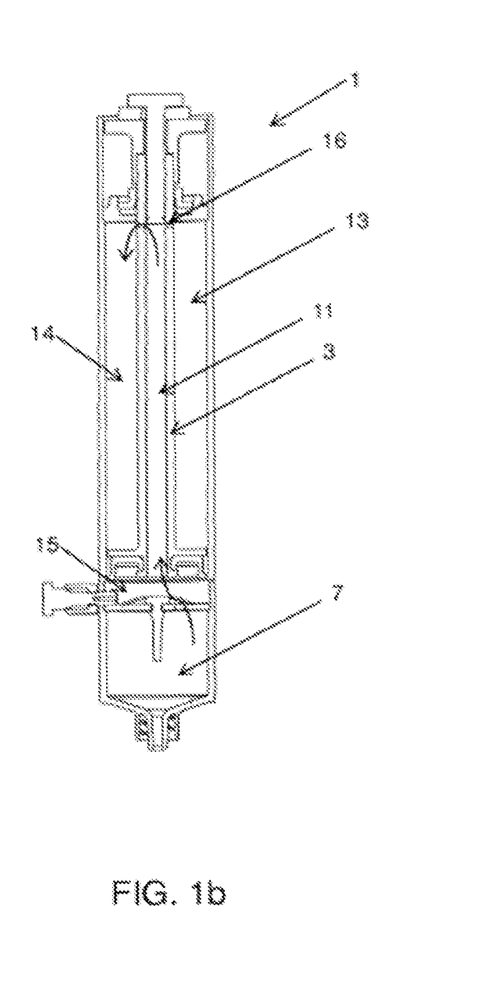
FIG. 1b shows the fine-needle aspiration syringe (1) of FIG. 1a in a second configuration for transporting air into the vacuum chamber (14).

As stated, the functionality of the inverted movement for creating a vacuum (i.e. pushing the plunger instead of pulling) involves the use of a plunger having a plunger head (9) sealingly engaged inside the barrel and a plunger body (10) with an internal channel (11). FIGS. 1a and 1b serve as an example of how the design may operate. In FIG. 1a, disclosing an embodiment according to the presently disclosed fine-needle aspiration syringe (1), the syringe (1) is configured to generate vacuum in the vacuum chamber (14) when the plunger is moved downwards in the figure (towards the distal end). When the plunger head (9) is pushed in the direction towards the distal end of the syringe, the vacuum chamber (14) is mechanically expanded. In this configuration the vacuum chamber (14) and the internal channel (11) are fluidly disconnected in relation to each other—the vacuum chamber (14) is a closed space in this configuration. When the vacuum chamber (14) expands, it will have a relative low pressure locally in the vacuum chamber (14). In this configuration, the air in the proximal lumen (7) is typically pushed out through the plunger body (10), leaving the syringe (1). The air may leave the internal channel (11) through an opening or side channel (16)

When the plunger is pushed beyond a predefined limit in the longitudinal direction of the syringe towards the distal end of the syringe, it enters the second configuration, wherein the vacuum chamber (14) and the internal channel (11) are fluidly connected, and wherein the internal channel (11) does not have a connection to the outside of the syringe anymore, as shown in FIG. 1b. This causes air to flow from the distal lumen (7) through the valve (8), further the internal channel (11) into the vacuum chamber (14), thereby also aspirating fluid and/or tissue through the opening of the distal end of the syringe (1) and/or first hollow needle (5).

Vacuum in the present disclosure shall not be construed as absolute vacuum but a decreased pressure inside the syringe that allows tissue to be aspirated.

In one embodiment, the plunger body (10) has a side channel (16) fluidly connecting the internal channel (11) and the vacuum chamber (14) in the second configuration of the syringe. In this embodiment, the side channel (16) may connect the internal channel (11) and the vacuum chamber (14) when the channel (16) is located on the distal side of the sealing element (13) and connects the internal channel (11) to atmospheric pressure when the side channel (16) is located on the proximal side of the sealing element (13).

Figure 2:
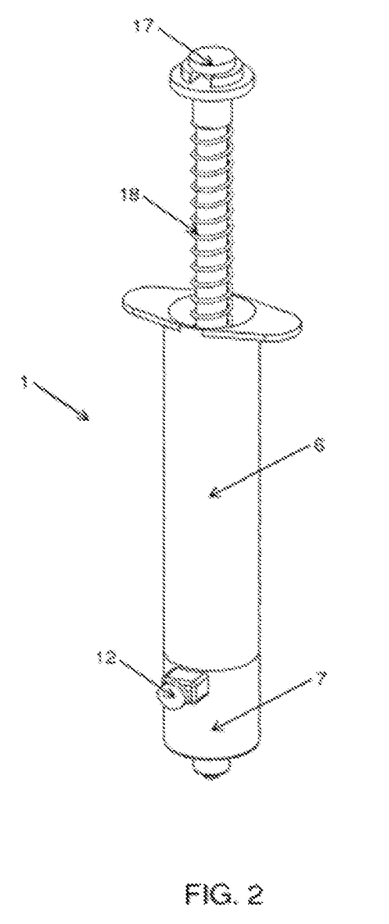
FIG. 2 shows one embodiment of the presently disclosed biopsy needle, in form of a fine-needle aspiration syringe (1) having a coil spring (18) for accumulative generation of vacuum.

As shown in e.g. FIGS. 1 and 2, the FNA syringe (1) may comprise a pressure element (17) at the proximal end of the plunger body (10). The pressure element can be pushed by a thumb to generate vacuum and aspirate using the presently disclose fine-needle aspiration syringe.

Vacuum Configuration—Exhaust Configuration

In the fine-needle aspiration syringe (1) according to the above description, the aspirated tissue and/or fluid will be aspirated and collected in the distal lumen (7). In a further embodiment, the fine-needle aspiration syringe (1) may, in addition to the aspiration functionality, be configured to exhaust the aspirated tissue and/or fluid in a controlled manner. Typically, when tissue and/or fluid has been collected, the syringe (1) is removed from the area and the aspirated tissue and/or fluid may then be deposited for e.g. examination and/or storage of a sample by exhausting the aspirated tissue and/or fluid from the distal lumen (7) through the tip (4). In one embodiment, distal lumen (7) is made of a transparent material. This allows that the user can see the tissue and/or fluid that has been collected, in order to decide whether more tissue/fluid is to be collected or whether the collected tissue/fluid is to be exhausted by venting the device.

In one embodiment, the fine-needle aspiration syringe (1) further comprising a valve switch element (12) for controlling the valve (8) such that air can only flow from the distal lumen (7) to the proximal lumen (6) in a vacuum configuration, and such that air can flow freely between the distal lumen (7) to the proximal lumen (6) in an exhaust configuration. In the vacuum configuration, air cannot flow from the proximal lumen (6) to the distal lumen (7), which can be achieved by using a one-way valve.

Figure 4:
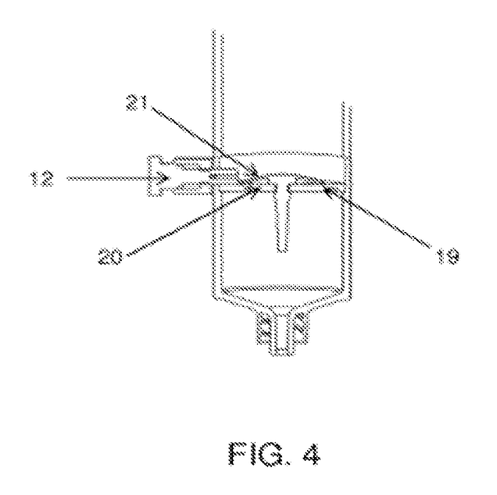
FIG. 4 shows one embodiment of the valve (8) between the proximal lumen (6) and the distal lumen (7).

There are several embodiments for achieving the vacuum configuration and exhaust configuration. In one embodiment, the valve (8) comprises a rigid part (19) having at least one hole (20) and a flexible membrane (21), wherein the membrane is flexible such that it covers the at least one hole (20) in the first valve configuration and that it does not cover the at least one hole (20) in the second valve configuration. The rigid part (19) may be shaped as a rigid disc. FIG. 4 shows an example of an embodiment having a flexible membrane (21). In this solution, when the switch element (12) asserts a sideways force on the flexible membrane (21), the membrane will bend such that it does not cover the hole (20), which will allow air to flow between the distal lumen (7) and the proximal lumen (6). When the plunger (3) is moved towards the distal end of the syringe, the content of the distal lumen (7) is pushed out of the syringe through the tip (4). In this embodiment, the valve switch element (12) controls the flexion of the flexible membrane (21) by asserting a force sideways.

Figure 5A:
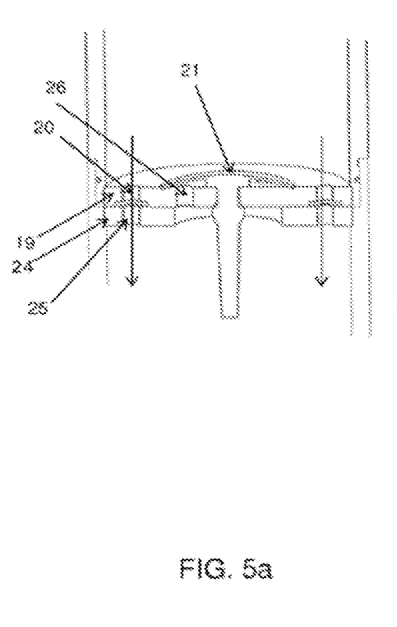
FIGS. 5a and 5b show another embodiment of the valve (8) between the proximal lumen (6) and the distal lumen (7).
Figure 5B:
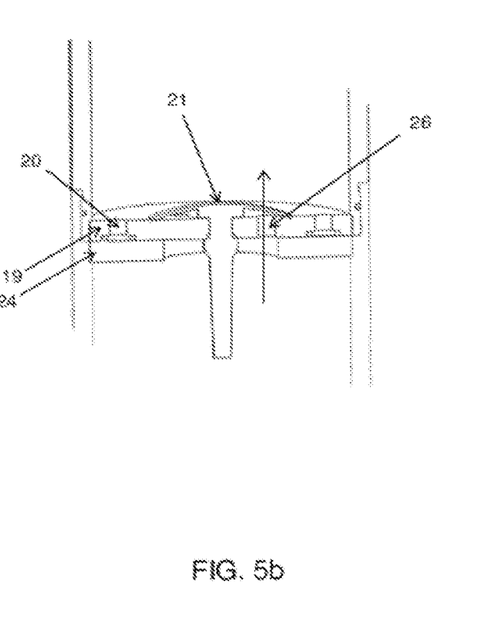

In a second embodiment of the exhaust mechanism, the rigid part (19) is a first disc (19), the valve (8) further comprising a second disc (24), wherein at least one of the discs is rotatable, each of the discs comprising at least one hole (20, 25), and wherein the holes (20, 25) are aligned in the exhaust configuration and not aligned in the vacuum configuration. An example of this embodiment is shown in FIGS. 5a and 5b.

In a further embodiment, the syringe (1) further comprises a spacing element (22) for preventing that the plunger (3) is moved beyond a predefined limit in the longitudinal direction of the syringe (1). The spacing element (12) may be placed between an extension element (23) e.g. as part of the plunger (3) and the pressure element (17).

Accumulative Generation of Vacuum

The present disclosure further relates to accumulative generation of vacuum in a syringe (1) by pushing and releasing the plunger (3) repetitively. For the purpose, the syringe (1) preferably comprises a coil spring (18), which may be located between the sealing element (13) and the pressure element (17) or the extension element (23) (or any part in fixed connection with the pressure element (17) or the element (23)).

The possibility for accumulative generation of vacuum introduces several benefits for the user. One advantage is that it is possible to obtain a higher level of vacuum by removing air repetitively. A further advantage is that instead of one long movement of the plunger, additional smaller movements can generate the same, which allows a shorter design of the syringe (1). It may also be more preferable from an ergonomic perspective of the user to use several short movements instead of one long movement.

By pushing the plunger (3) towards the distal end of the syringe (1) and releasing it towards the proximal end of the syringe (1) repetitively, a vacuum is accumulated. The syringe may either be open in the distal end, thereby aspirating additional tissue and/or fluid for every stroke (or accumulating the vacuum until the aspirating force is greater than a limit required for starting the process of drawing tissue into the distal lumen (7)), or, if the syringe is closed in the distal end, an accumulated vacuum may be generated inside the distal lumen (7), which is released when the distal end is opened. In one embodiment, the syringe (1) further comprises a vacuum release element (27) at the distal end of the syringe (1) for maintaining and releasing a vacuum generated in the distal lumen (7) through a tip (4). In this way, a vacuum may be generated by one or several strokes while the vacuum release element (27) is closed such that there is no connection between the distal lumen (7) and the exterior environment of the syringe (1) through the tip (4). When a suitable level of vacuum has been generated in the distal lumen (7), which may thereby serve as an accumulator tank in this configuration, the vacuum release element (27) may be opened such that the distal lumen (7) is in fluid connection with the external environment of the syringe (1) (typically when a first hollow needle (5) is inserted to an area from which fluid and/or tissue is to be collected), thereby using the generated vacuum to aspirate the fluid and/or tissue into the distal lumen (7).

The syringe (1) may further comprise an activation switch for controlling the vacuum release element (27). The activation may be placed directly on or adjacent to the vacuum release element (27), but can also, more conveniently, be placed at the proximal end of the fine-needle aspiration syringe (1). Since the user typically has the thumb on a pressure element (17), the activation switch may be located e.g. on the pressure element.

In relation to the possibility to switch between the syringe (1) being closed an open in the distal end, the syringe may be used in a number of scenarios involving "loading" the syringe (1), which is to be construed as generating a vacuum, which is not immediately released. In one embodiment, the fine-needle aspiration syringe (1) therefore has a loaded configuration, wherein the vacuum release element (27) maintains the tip (4) of the syringe (1) in a closed position (e.g. by blocking the passage in the tip) and a generated vacuum is held in the barrel (2), and a released configuration, wherein the vacuum release element (27) is maintains the tip (4) of the syringe (1) in an open position.

In one scenario, the syringe may be loaded with a vacuum as described before the first hollow needle (5) is inserted into the area from which fluid and/or tissue is aspirated. This has the advantage that the generation of vacuum can be done without the risk of moving the first hollow needle (5) inside the patient. Once the vacuum has been generated, i.e. the syringe (1) has been loaded, the needle can be carefully inserted, preferably without having to push or press any buttons. Once the first hollow needle (5) has been positioned, the vacuum release element (27) can be changed from closed to open (e.g. by using an activation switch), which causes the vacuum inside the barrel (2) to aspirate fluid and/or tissue into the distal lumen (7). The "loading" may include both a single stroke to generate vacuum or several strokes to accumulate a vacuum as described.

Alternatively, or in combination with this approach, the loading function can be used when the first hollow needle is already located in the area from which fluid and/or tissue is to be aspirated. In this example, the vacuum that is generated inside the barrel (2) can either be used immediately to aspirate tissue—in this case the vacuum release element (27) maintains the tip (4) in an open position—or can be maintained in a closed position in order to accumulate a suitable level of vacuum, and then released. This procedure may be repeated.

The syringe (1) may also further comprise a mechanism for releasing a generated vacuum step-wise in predetermined steps. As an example, when the syringe (1) has been loaded, a button (29) can be used to release only a part of the generated vacuum. Such a mechanism may be useful in several scenarios, e.g. for testing whether the syringe (1) is well positioned or has the correct level of vacuum. This function can be implemented for example as a step-wise release element (e.g., button 29) configured to release a part of the generated vacuum, such as 20% of the vacuum, when pressed, corresponding to the plunger head (9) moving a part of the distance between the valve (8) and sealing element (13).

The vacuum accumulation mechanism and process can be further described as follows: In a first position, the plunger is placed in a retracted position i.e. plunger (3) closer to the proximal end of the syringe (1). As described above, when the plunger is moved in the direction towards the distal end of the syringe (1), a vacuum is created in the vacuum chamber (14), and when the plunger is pushed beyond a predefined limit in the longitudinal direction of the syringe towards the distal end of the syringe, it enters the second configuration, wherein the vacuum chamber (14) and the internal channel (11) are fluidly connected, and wherein the internal channel (11) does not have a connection to the outside of the syringe anymore, as shown in FIG. 1b. If the user then releases the pressure element (17), the coil spring (18) moves the plunger back to the retracted position. Preferably, in this embodiment, the sealing element (13) comprises a one-way valve (30) allowing air to exit the vacuum chamber (14) through sealing element (13) when the plunger (3) is retracted. From the retracted position, the plunger can then be pushed towards the distal end of the syringe (1) again, thereby building up further vacuum in the distal lumen (7) and/or aspirating further tissue and/or fluid.

Since, in one embodiment, the internal channel (11) will, during certain phases of the repeated procedure of generating vacuum be in fluid connection with atmospheric pressure, i.e. there will be a certain amount of air inside the internal channel (11) when the syringe (1) enters the first configuration. Therefore, in one embodiment, the volume of the internal channel (11) in the presently disclosed fine-needle aspiration syringe (1) is smaller than the volume of the vacuum chamber (14). Preferably, the volume of the vacuum chamber (14) is significantly larger than the volume of the internal channel (11), such as at least twice as large as the volume of the internal channel (11), more preferably at least three times as large, even more preferably at least five times as large, most preferably at least ten times as large.

Second Hollow Needle

As stated, the presently disclosed fine-needle aspiration syringe may comprise a removable needle. The fine-needle aspiration syringe may be further arranged with a second hollow needle (28) configured to guide the first hollow needle (5). The second hollow needle (28) may act as a "fixed" channel through which the first hollow needle (5) operates. One advantage with such a configuration is that once a sampling location has been found, it is possible to keep the second hollow needle (28) in this position, whereas the first hollow needle (5) on the syringe (1) can be inserted for aspirating fluid/tissue, then removed e.g. for exhausting the sampled tissue/fluid, and then re-inserted through the same channel (second hollow needle (28)) without removing the second hollow needle (28).

In a further embodiment, the second hollow needle (28) is configured to leave a marking in the area where tissue/and or fluid is aspirated. By leaving a marking that can be tracked through e.g. different scanning techniques, it can, after the aspiration of fluid/tissue, be verified that the tissue/fluid has been aspirated from the correct location.

EXAMPLES

The invention will in the following be described in greater detail with reference to the accompanying drawings. The drawings are exemplary and are intended to illustrate some of the features of the presently disclosed fine-needle aspiration syringe for aspirating fluid and/or tissue, and are not to be construed as limiting to the presently disclosed invention.

FIG. 1a shows a cross-section of an example of the presently disclosed fine-needle aspiration syringe (1) for aspirating fluid and/or tissue in a first configuration for establishing vacuum in the vacuum chamber (14). The syringe (1) comprises a barrel (2) having a proximal lumen (6) and a distal lumen (7). The syringe (1) further comprises a plunger (3) having a plunger head (9) and a plunger body (10) with an internal channel (11). There is a tip (4) to which a first hollow needle may be attached. The tip may be closed and/or sealed in one configuration if needed. The syringe (1) of the example further comprises a valve (8) located between the plunger head (9) and a distal end of the syringe inside the barrel (2), separating the proximal lumen (6) and the distal lumen (7). The valve (8) comprises a rigid part (19) in the shape of a disc comprising a hole (20). The syringe (1) further comprises a valve switch element (12) for controlling the valve (8). There is also a sealing element (13) inside the barrel on the proximal side of the plunger head (9) making sure that the space behind the plunger head (9) (i.e. the vacuum chamber (14)) is a sealed space. Between the plunger head (9) and the valve (8) (which may be a one-way valve) there is a space which may be referred to as a variable proximal lumen volume (15), variable since the position of the plunger head (9) determines the volume. In the example, the plunger body (10) has a side channel (16). The syringe (1) also has a pressure element (17) to be pressed in order to move the plunger towards the proximal end of the syringe (1). FIG. 1b shows the fine-needle aspiration syringe (1) of FIG. 1a in a second configuration for transporting air into the vacuum chamber (14). In this configuration the side channel (16) connects the vacuum chamber (14) and the internal channel (11).

FIG. 2 shows one embodiment of the presently disclosed fine-needle aspiration syringe (1) having a coil spring (18) for accumulative generation of vacuum. The coil spring (18) is placed under the pressure element (17) and the sealing element (not shown) inside the barrel. The syringe (1) further comprises a valve switch element (12) for controlling the valve (not shown) inside the syringe. The barrel is divided into a proximal lumen (6) and a distal lumen (7).

Figure 3A:
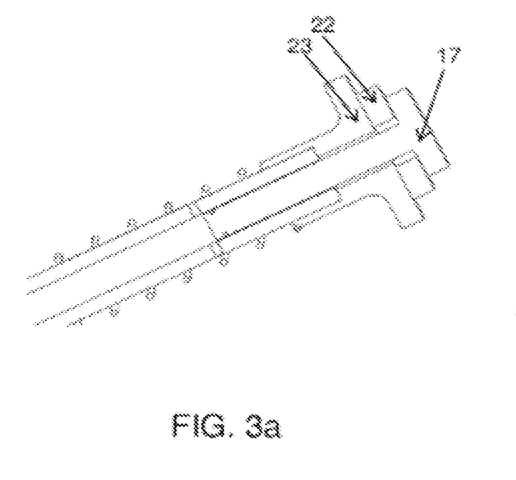
FIGS. 3a and 3b show an example of the functionality of a spacing element (22) for controlling the maximum movement of the plunger (3) inside the barrel (2).
Figure 3B:
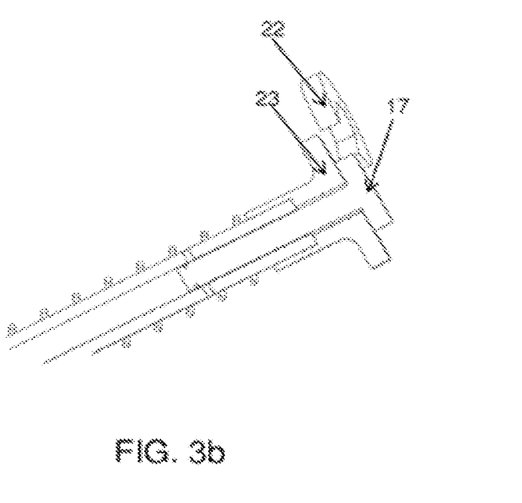

FIGS. 3a and 3b show an example of the functionality of a spacing element (22) for controlling the maximum movement of the plunger (3) inside the barrel (2). In FIG. 3a the spacing element (22) is positioned between the pressure element (17) and the extension element (23) which is part of the plunger body (10). In FIG. 3b the spacing element (22) has been removed from the blocking position such that pressure element (17) can be positioned further towards the distal end of the syringe.

FIG. 4 shows one embodiment of the valve (8) between the proximal lumen (6) and the distal lumen (7). The valve (8) has a disc (19) comprising a hole (20) and a flexible membrane (21). When the switch element (12) asserts a sideways (e.g. perpendicular to the longitudinal orientation of the syringe) force on the flexible membrane (21), the membrane bends such that it does not cover the hole (20), which allows air to flow freely in both directions of the valve.

FIGS. 5a and 5b show an alternative embodiment of the valve (8) between the proximal lumen (6) and the distal lumen (7). The valve (8) comprises a first disc (19) and a second disc (24). The first disc (19) has a hole (20) and the second disc (24) has a hole (25). At least one of the discs is rotatable, or the discs are rotatable in relation to each other. In FIG. 5a the holes of the two discs are aligned such that air can flow freely between the proximal lumen (6) and the distal lumen (7), corresponding to the second valve configuration. In FIG. 5b the holes of the two discs are positioned such that air cannot flow through the holes. However, the first disc (19) also has an inner hole (26) covered by the membrane (21), which may act as a one-wat valve, allowing air can to flow from the distal lumen (7) to the proximal lumen (6) in the first valve configuration.

Figure 6:
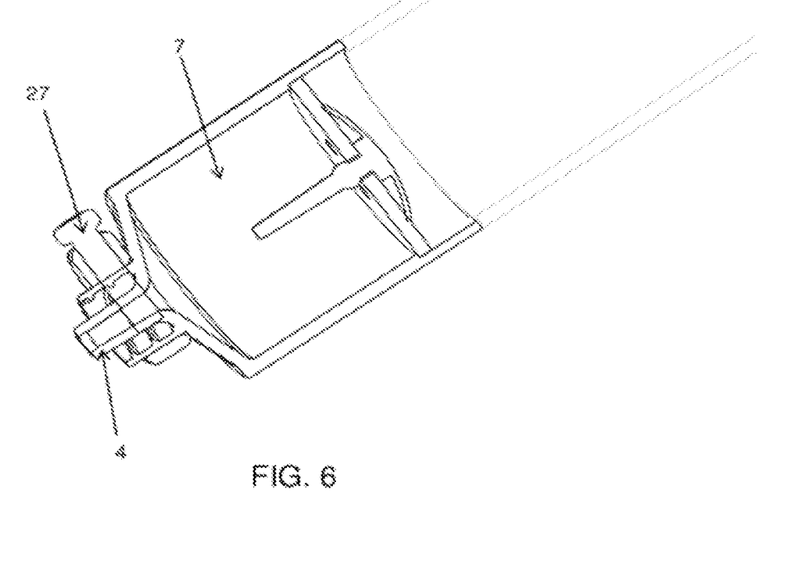
FIG. 6 shows the distal end of one embodiment of the fine-needle aspiration syringe (1) having a vacuum release element (27) for maintaining and releasing a vacuum generated in the distal lumen (7).

FIG. 6 shows a distal end of one embodiment of the presently disclosed fine-needle aspiration syringe (1) for aspirating fluid and/or tissue having a vacuum release element (27). The vacuum release element (27) can be used to block the passage (28) in the tip (4) of the syringe (1). In FIG. 6 the vacuum release element (27) is in a closed position such that the distal lumen (7) is sealed towards the outside (external environment) of the syringe through the tip (4). If the vacuum release element (27) is retracted from the passage (28), there is a fluid connection between the distal lumen (7) and the external environment of the syringe (7) through the tip (4).

The invention claimed is:

1. A syringe for extracting fluid and/or tissue comprising:
   a barrel having:
      a proximal lumen comprising a variable proximal lumen volume; and
      a distal lumen for collecting aspirated fluid or tissue;
   a plunger having:
      a plunger head sealingly engaged inside the barrel; and
      a plunger body with an internal channel;
   a valve located between the plunger head and a distal end of the syringe inside the barrel, separating the proximal lumen and the distal lumen such that air can only flow from the distal lumen to the variable proximal lumen volume in a first valve configuration to cause the fluid or tissue to collect in the distal lumen during use, wherein the variable proximal lumen volume is defined by a volume that varies between the valve and the plunger head when the plunger head is moved in a longitudinal direction of the syringe;
   a sealing element located inside the barrel proximal to the plunger head, wherein a volume between the plunger head and the sealing element define a vacuum chamber having a variable volume therebetween,
      wherein the vacuum chamber and the internal channel are fluidly disconnected in relation to each other in a first configuration of the syringe and fluidly connected in a second configuration of the syringe.

2. The syringe according to claim 1, the plunger body having a side channel fluidly connecting the internal channel and the vacuum chamber in the second configuration of the syringe.

3. The syringe according to claim 2, wherein the side channel connects the internal channel and the vacuum chamber when the side channel is located on the distal side of the sealing element and connects the internal channel to atmospheric pressure when the side channel is located on the proximal side of the sealing element.

4. The syringe according to claim 1, further comprising a pressure element at the proximal end of the plunger body.

5. The syringe according to claim 4, further comprising a coil spring between the sealing element and the pressure element.

6. The syringe according to claim 1, configured such that repetitively pushing the plunger towards the distal end of the syringe and releasing it towards the proximal end of the syringe accumulates a vacuum.

7. The syringe according to claim 6, wherein the sealing element comprises a one-way valve allowing air to exit the vacuum chamber when the plunger is retracted.

8. The syringe according to claim 1, further comprising a spacing element for preventing that the plunger is moved beyond a predefined limit in the longitudinal direction of the syringe.

9. The syringe according to claim 1, further comprising a vacuum release element at the distal end of the syringe for maintaining and releasing a vacuum generated in the distal lumen through a tip.

10. The syringe according to claim 9, in a loaded configuration, the vacuum release element is configured to maintain the tip of the syringe in a closed position and maintain a generated vacuum in the barrel, and wherein, in a released position, the vacuum release element is configured to maintain the tip of the syringe in an open position.

11. The syringe according to claim 1, further comprising an element configured to release a generated vacuum stepwise in predetermined steps.

12. The syringe according to claim 1, wherein the volume of the internal channel is smaller than the volume of the vacuum chamber.

13. The syringe according to claim 1, wherein the syringe is a fine-needle aspiration syringe.

14. The syringe according to claim 1, wherein the syringe is a core-needle biopsy syringe.

* * * * *